United States Patent [19]

Grippi

[11] Patent Number: 5,634,474
[45] Date of Patent: Jun. 3, 1997

[54] BLOOD COLLECTION ASSEMBLY INCLUDING CLOT-ACCELERATING GLASS INSERT

[75] Inventor: Nicholas A. Grippi, Ramsey, N.J.

[73] Assignee: Becton, Dickinson and Company, Franklin Lakes, N.J.

[21] Appl. No.: 431,199

[22] Filed: Apr. 28, 1995

[51] Int. Cl.[6] ................................................ A61B 5/00
[52] U.S. Cl. ................................................ 128/763; 128/765
[58] Field of Search .................... 128/760, 763–766, 128/770

[56] References Cited

U.S. PATENT DOCUMENTS

| | | | |
|---|---|---|---|
| 4,134,512 | 1/1979 | Nugent | 128/764 |
| 4,256,120 | 3/1981 | Finley | 128/763 |
| 4,420,517 | 12/1983 | Ali | 428/35 |
| 4,690,153 | 9/1987 | Losada et al. | 128/763 |
| 5,246,666 | 9/1993 | Vogler et al. | 422/73 |
| 5,326,535 | 7/1994 | Vogler et al. | 422/102 |
| 5,378,431 | 1/1995 | Vogler et al. | 422/73 |

*Primary Examiner*—Max Hindenburg
*Attorney, Agent, or Firm*—Richard E. Brown

[57] ABSTRACT

A blood collection assembly includes a tube, preferably plastic, an elastomeric stopper and a siliceous insert immobilized in the tube under the stopper. In a method for taking a blood sample using the assembly, the stopper is punctured and the sample is discharged onto the insert to initiate clotting.

7 Claims, 5 Drawing Sheets

BLOOD COLLECTION ASSEMBLY INCLUDING CLOT-ACCELERATING GLASS INSERT

BACKGROUND OF THE INVENTION

1. Field of the Invention

This invention relates to blood collection and, more particularly, relates to a plastic blood sample collection assembly.

2. Background

Blood samples are routinely taken in evacuated tubes, such as glass VACUTAINER™ brand tubes (Becton, Dickinson and Company). One end of a double-ended needle is inserted into a patient's vein. The other end of the needle then punctures a stopper covering the open end of the VACUTAINER™ tube so that the vacuum in the tube draws the blood sample through the needle into the tube. Using this technique, a plurality of samples can be taken using a single needle puncture of the skin.

Plastic tubes have also been proposed for blood collection. Plastic offers a number of advantages over glass such as lower breakage, less weight in shipment, and easier disposal by incineration.

Blood collected in evacuated tubes often must be clotted prior to clinical examination. It is desirable to form a dense clot as rapidly and completely as possible to facilitate clean separation of the clot from the serum layer by centrifugation. To achieve this end, both plastic and glass blood collection tubes frequently employ a clot activator. Typical activators are diatomaceous earth and particles of inorganic silicates, or biochemicals such as ellagic acid, thrombin and thromboplastin. In one line of commercial blood collection tubes, for example, a coating of silica particles in polyvinylpyrrolidone (PVP), a water soluble polymer, is affixed to the inside of the tube. When blood enters the tube, the PVP dissolves and silicate particles are released to initiate clotting. The PVP enters both the serum and clot.

A problem with particulate activators is that finely divided particles must be mixed by multiple inversions, may not pellet completely with the clot and may thus contaminate the serum layer and interfere with certain blood analyses. In addition, particles suspended in the serum may foul automatic blood analyses instruments. On the other hand, soluble biochemical activators are disadvantageous because these cannot be easily separated from either the serum or blood clot and can interfere with both chemical and serological assays. In particular, for highly specialized applications, such as blood banking, it is advantageous to avoid either soluble activators or particulates in the cell mass of a blood clot because these cells are used in blood typing analyses. For this reason, samples for blood banking are routinely taken in glass tubes and rely on the clot activating property of the glass to induce clotting.

There is a need in the art of blood collection for equipment which provides an enhanced rate of blood coagulation without leaving any soluble or particulate material in the serum layer or in the clot on centrifugation, thus avoiding potential interference with clinical tests, and particularly in blood banking procedures. The present invention is directed to fulfilling this need.

SUMMARY OF THE INVENTION

A blood collection assembly includes a tube of glass or preferably plastic having a bottom wall continuous with a side wall. The side wall defines an open end and the bottom wall defines a closed end. Together the bottom and side walls define an inside wall surface. The open end is covered by a puncturable stopper and the tube preferably is evacuated.

The assembly includes a clot activating siliceous insert immobilized within the interior volume of the tube by permanent or movable affixation to the stopper or tube wall. In this disclosure the term siliceous includes any material consisting partially or predominantly of silica. The term movably affixed means that the insert is immobilized in the interior volume until it descends on centrifugation. The insert may be of various shapes, such as a capillary, funnel, disc, cover slip, woven fabric or monofilament. An additive useful in blood separation or analysis procedures may be present in the tube.

When a blood sample is taken in the assembly of the invention, the blood flows past and comes into contact with the insert. This contact activates the clotting cascade.

Thus the assembly of the invention retains the advantages of plastic for tube construction and overcomes the disadvantage of poor and slow coagulation in plastic. Blood is delivered from the needle directly into contact with the insert to activate clotting, but no particulate or soluble clotting activators or binders are present to contaminate either the serum or the clot, and no mixing is required to ensure clotting rate or quality.

DETAILED DESCRIPTION

While this invention is satisfied by embodiments in many different forms. there will herein be described in detail embodiments of the invention with the understanding that the present disclosure is to be considered as exemplary of the principles of the invention and is not intended to limit the invention to the embodiments illustrated and described. The scope of the invention will be measured by the appended claims and their equivalents.

Figure 1:
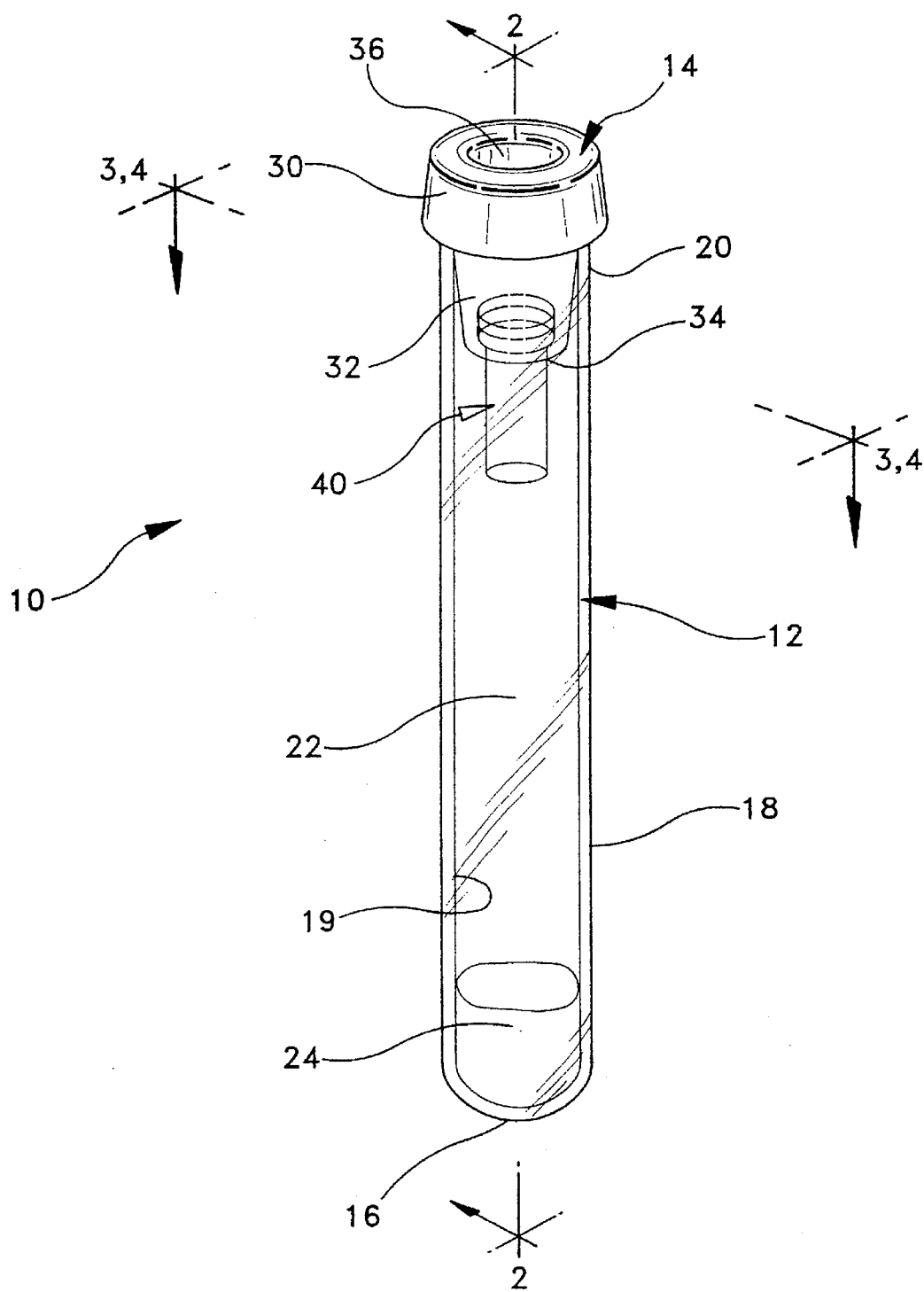
FIG. 1 is a perspective view of the blood collection assembly of the invention.
Figure 2:
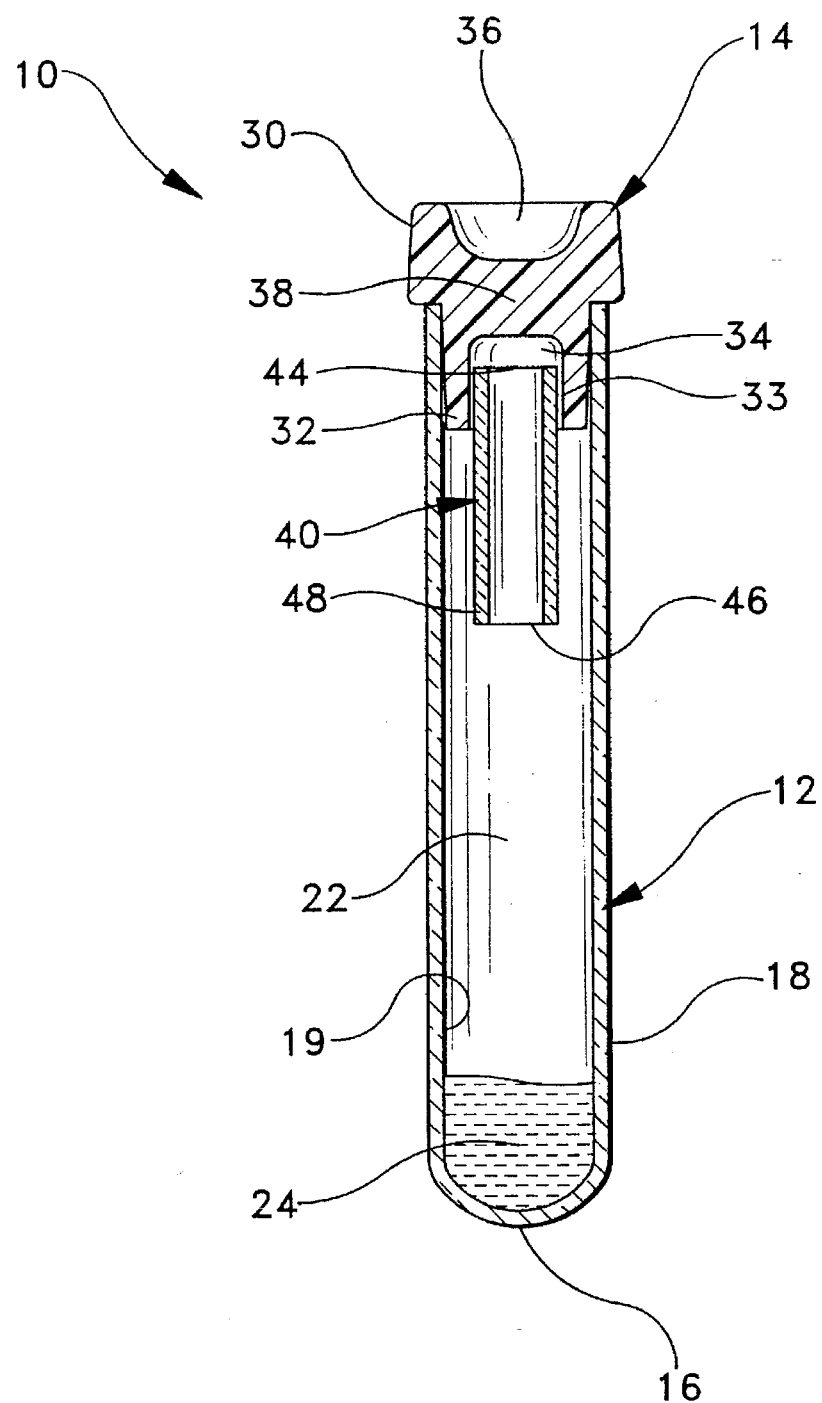
FIG. 2 is a vertical sectional view of the assembly of FIG. 1 taken along the line 2—2 thereof.
Figure 3:
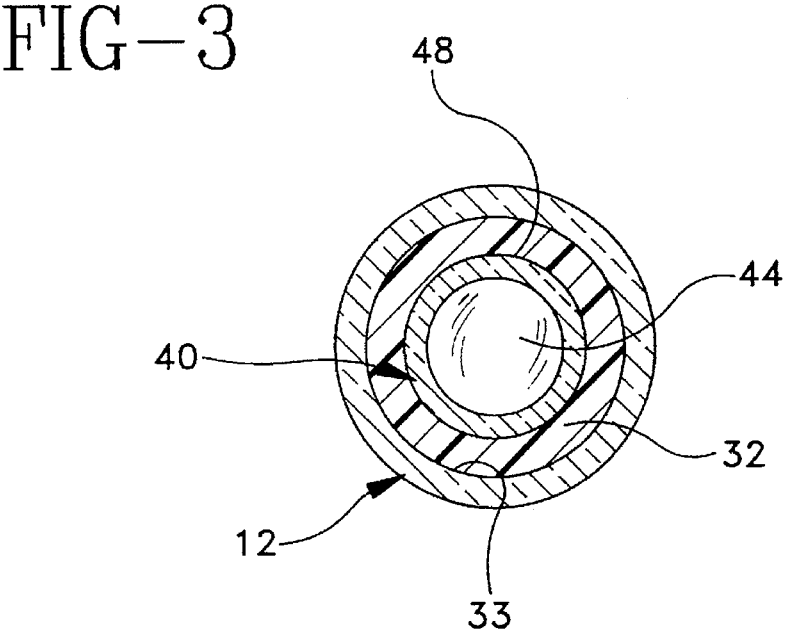
FIG. 3 is a horizontal sectional view of the assembly of FIG. 1 taken along the line 3—3 thereof.

The blood collection assembly of the invention may include any container having a closed end and an open end. Suitable containers are, for example bottles, vials, flasks and the like, preferably tubes. The invention will hence forth be described in terms of the preferred evacuated blood collection tube. Adverting now the drawings, FIGS. 1 to 3 illustrate a blood collection assembly 10 which includes a tube 12 and a puncturable stopper 14. Tube 12 has a bottom wall 16 and a side wall 18 having an inside wall surface 19. Side wall 18 defines an open end 20 into which stopper 14 may be placed. Bottom wall 16, side wall 18 and stopper 14 enclose an interior volume 22 of the tube which preferably contains a conventional serum separating gel 24 and preferably is evacuated. Evacuated tubes for blood collection are standard in the art.

Stopper 14 includes an annular upper portion 30 which extends over the top edge of side wall 18 and a lower annular portion or skirt 32 which extends into and forms an interference fit with inside wall surface 19 for maintaining stopper 14 in place in open end 20. Annular skirt 32 has an inner side wall 33 which defines a well 34. Annular upper portion 30 defines a cavity 36. A septum portion 38 of annular upper portion 30 extends between well 34 and cavity 36 for puncture by a cannula (as described below). One or more capillary inserts 40 having open top end 44, open bottom end 46 and side wall 48 may be immobilized in well 34.

Figure 4A:
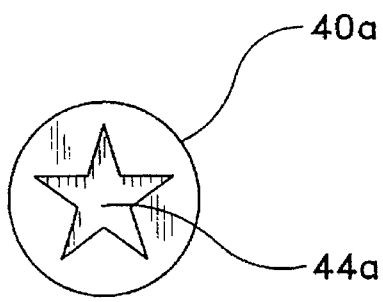
FIG. 4a and 4b are alternative embodiments of the capillary of the assembly.
Figure 4B:
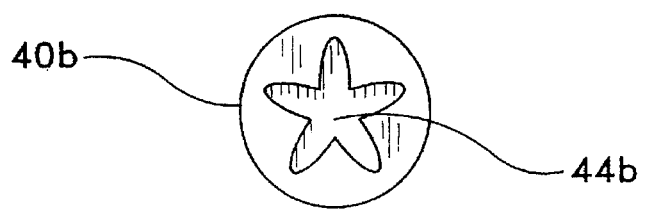

Preferred capillaries for the above-described standard blood collection tubes may be of glass tubing. Preferred tubing may be about 0.5–11.0 cm in length, 0.2–3.0 mm inside diameter and 3.0–10.0 mm outside diameter. These dimensions allow the capillary to fit into the well within the skirt portion of conventional blood collection tube stoppers with an axial orientation for accessibility to the blood draw cannula. However, no criticality is associated with the capillary length and diameter, and one skilled in the art may easily construct a capillary of other dimensions and a tube stopper to fit. Likewise, the capillary need not have the circular shape shown in FIGS. 1 to 3. For example, FIG. 4a and 4b illustrate other suitable capillary shapes 44a and 44b which have the advantage of providing more surface area for blood contact that the circular capillary of FIGS. 1 to 3. (In FIGS. 4–10 elements similar to those previously described are given the same reference number followed by a letter suffix).

Figure 5:
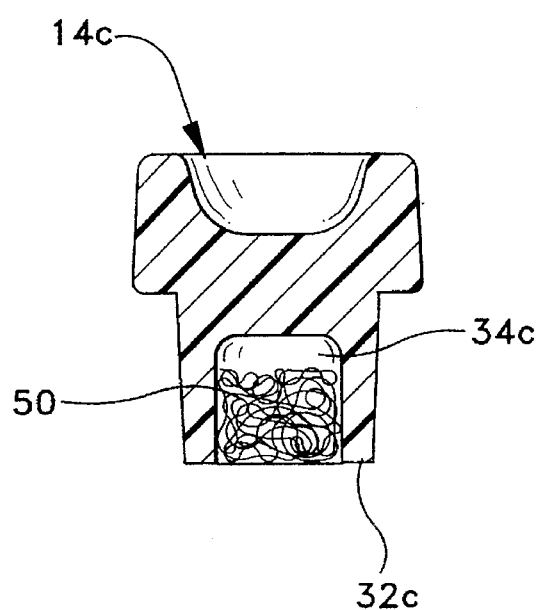
FIGS. 5–8 are embodiments of the assembly having monofiliment wad, disc, funnel and cover slip inserts respectively.
Figure 6:
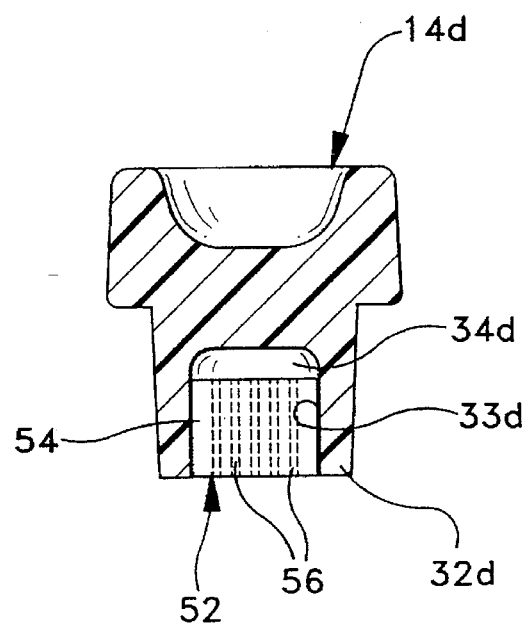
Figure 7:
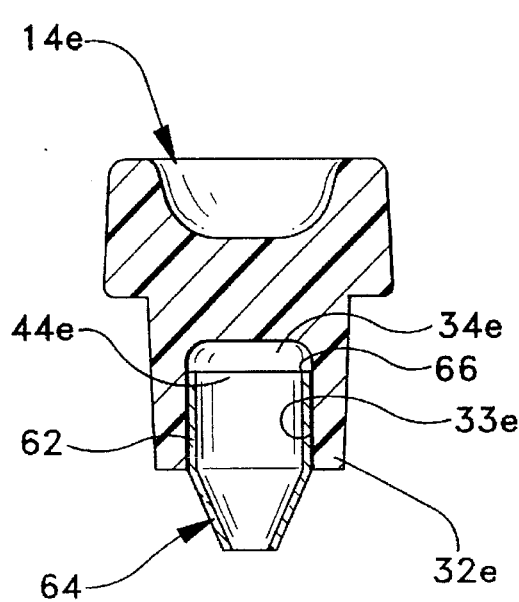
Figure 8:
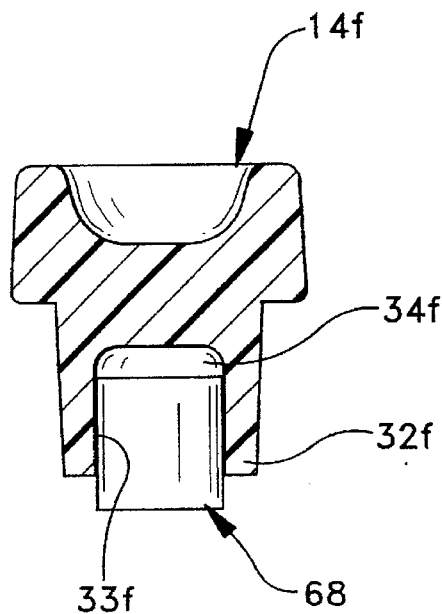

The insert need not be a capillary at all. In FIG. 5, a wad a glass monofilament 50 may be wedged into well 34c of stopper 14c. Blood delivered from the cannula passes through the wad to initiate clotting. In FIG. 6, the insert is a perforated disc 52 having a side wall 54 which is immobilized in the well by an interference fit between side wall 54 and inner skirt side wall 33d. Disc 52 has a plurality of channels 56 therethrough for passage of the blood sample wherein contact of the blood with the channel side wall initiates clotting. Channels 56 while shown in FIG. 6 to be substantially circular, may be of any shape, size and number. Thus the disc and channels together may be substantially in the form of a woven fabric or filter disc of siliceous material. It is readily seen that the plurality of channels 56 serve the same purpose as capillary open end 44 of FIGS. 1–3. FIG. 7 shows the insert in the shape of a funnel 60. Funnel 60 has an upper side wall portion 62, a lower tapered side wall portion 64 and a top wall 66 which defines open top end 44e through which the blood sample passes. Upper side wall portion 62 forms an interference fit with inner side wall 33e of skirt portion 34e. The insert may be a glass cover slip. FIG. 8 illustrates cover slip 68 interference fitted against inner side wall 33f of annular skirt 32f.

As mentioned above, the insert may preferably be immobilized in the stopper well by an interference fit. The fit may be sufficiently tight that the insert. is permanently immobilized, or it may be sufficiently loose so that the insert is released during centrifugation and descends to become part of the clot.

Figure 9:
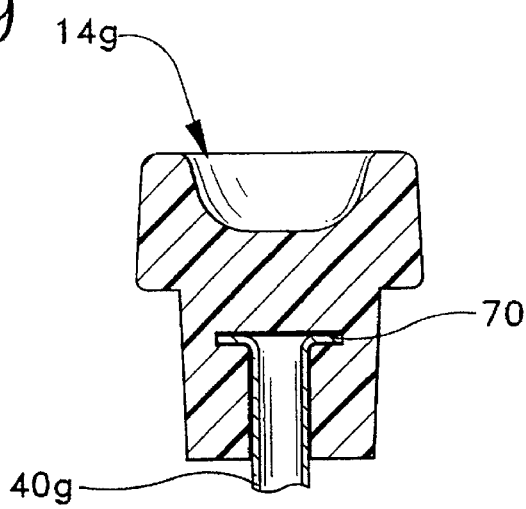
FIGS. 9–11 illustrate alternative arrangements for immobilization of the insert in the assembly.
Figure 10:
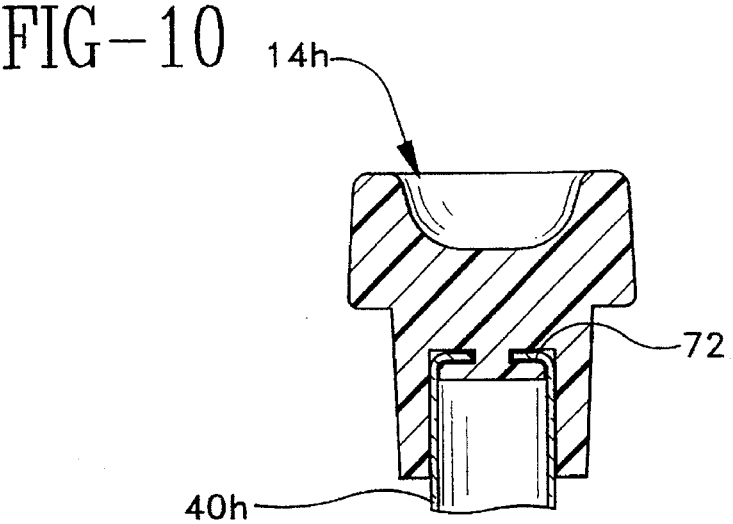
Figure 11:
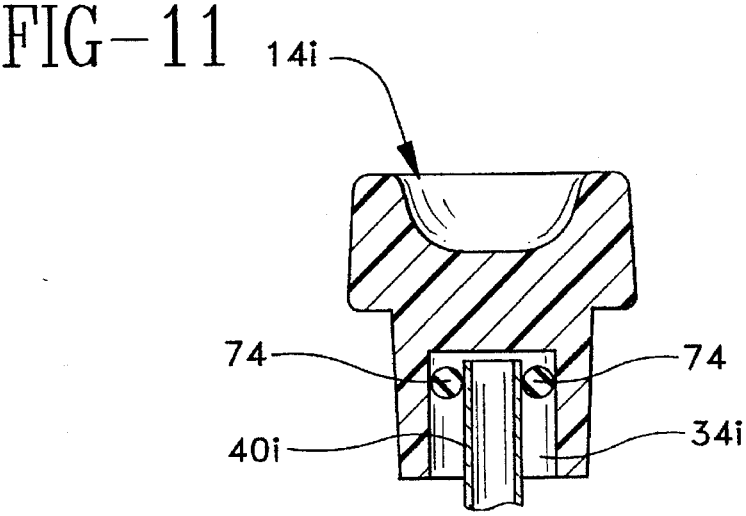

Without wishing to be limited thereby, a variety of alternative designs for immobilization of the insert in the stopper well are contemplated by the invention. For example, FIGS. 9 and 10 illustrate capillaries 40g and 40h to have outwardly and inwardly pointing lips 70 and 72 respectively which mate with modified stoppers 14g and 14h respectively. In FIG. 11, capillary 40i is immobilized in well 34i by an elastomeric O-ring 74.

While the above description is directed to the invention having a capillary insert interference-fitted into the stopper well, it is readily seen that the insert may easily be permanently or movably affixed to the tube wall by any conventional means such as an O-ring or by routine modification of the stopper or tube wall.

The tube may be of glass or preferably plastic. Suitable plastics are polypropylene, polyethylene terephthalate and polystyrene. While the tube may be of any size, the invention is particularly well suited to evacuated blood collection tubes. These tubes are generally cylindrical, 50 to 150 mm in length and about 10 to 20 mm in diameter. The stopper may be of any elastomer or laminate/composite, as is well known in the art of evacuated blood collection equipment.

Exemplary of suitable siliceous material for construction of the insert are silica, silicates, diatomaceous earth and preferably glass or quartz.

The assembly may contain, depending on the projected end use, any of a variety of additives known to be useful in blood separation or analysis. A preferred additive is a thixotropic gel which, on centrifugation of the tube, migrates to the interface between the serum and the cells and serves for separation. A procoagulant, such as elagic acid, fibrinogen or thrombin may be included to augment the clot activating effect of the insert.

In its preferred application, the assembly of the invention is used for collection of a blood sample and separation of the sample into a serum layer and a pellet of clotted cells. A patient sample is drawn through a double ended needle into the evacuated tube by puncture of the stopper. The sample comes into contact with the siliceous insert which activates the clotting mechanism. After allowing a few minutes for clotting, the tube is centrifuged to give the serum layer and the pellet separated by the gel.

In another embodiment of the invention, it has been found that treatment of the interior wall surface of the tube with a plasma results in a further increase in the rate of clotting of a blood sample. The plasma may be generated from any suitable process gas. A representative but not limiting list of suitable process gasses includes nitrogen, ammonia, carbon dioxide, sulfur dioxide, air and oxygen wherein air and oxygen are preferred. A conventional plasma generator equipped with electrodes and power source, a pressure gauge, a gas inbleed and a vacuum connection may be used. Any suitable ionizing plasma may be used, as, for example, a plasma generated by a corona discharge or preferably a glow discharge.

A wide range of power settings, power source frequencies and duration of exposure of the plastic surface to the plasma may be used. Ranges for these parameters which provide advantageous results are DC or AC power levels up to 200 watts, about 0.1 to about 50 megahertz and about 0.1 to 30 minutes. Preferred ranges are 10–50 watts, 10–20 megahertz and 2–10 minutes respectively. Any gas pressure may be used, however, gas pressures are advantageously maintained at 5 mm of Hg or below in order to benefit from reduced voltage requirements. Ambient temperature for plasma generation is preferred. Further details are not needed by one skilled in the art for a full understanding of this aspect of the invention.

EXAMPLE

Using a double ended needle, blood was drawn from 6 donors and directed through glass capillaries of 0.1 cm diameter and the lengths given in the table balow. The blood was collected in polypropylene tubes and clotting times were measured without inversion and compared with clotting time observed after 5 inversions with commercial glass tubes (Bedon, Dickinson and Company SST™ tubes with silica activator). Results are given in the following chart:

| Donor No. | Capillary length (cm) | Clotting Time (Min) | |
|---|---|---|---|
| | | Plastic | SST™ |
| 1 | None | 21 | 12 |
| 2 | 1.27 | 12 | 6 |
| 3 | 1.27 | 16 | 8 |
| 4 | 5.08 | 8 | 7 |
| 5 | 10.16 | 13 | 11 |
| 6 | 10.16 | 7 | 8 |

It is seen that the capillary significantly reduces the clotting time, and the plastic tube with a capillary clots in approximately the same time (7–16 minutes) as the current commercial glass tube with silica activator (12 minutes).

What is claimed is:

1. A blood collection assembly comprising:
   a) a container having a bottom wall and a side wall defining an open end;
   b) a stopper in said open end, said bottom wall, side wall and stopper defining an interior volume of said container; and
   c) a clot activating siliceous insert permanently immobilized by an interference fit within said stopper.

2. The assembly of claim 1 wherein said container is evacuated.

3. The assembly of claim 1 wherein said stopper is puncturable.

4. The assembly of claim 1 further comprising a serum-separating gel in said interior volume.

5. The assembly of claim 1 wherein said insert is a capillary, cover slip, funnel, glass monofilament, perforated disc or woven fabric.

6. A blood collection assembly comprising an evacuated plastic tube having a bottom wall, a side wall defining an open end, a puncturable stopper in said open end, said stopper including annular upper and lower portions, said lower portion defining a well, and a siliceous clot-activating insert permanently immobilized by an interference fit with a side wall of said well.

7. A method for collecting a sample of blood for analysis using the assembly of claim 1 comprising:

a) puncturing the stopper of claim 1 with a needle connected to a blood sourcel;

b) directing blood flowing through said needle into contact with the insert of claim 1 to induce clotting of said blood; and c) centrifuging said container to separate clotted blood from serum or plasma.

* * * * *